(12) United States Patent
Till

(10) Patent No.: US 7,497,237 B2
(45) Date of Patent: Mar. 3, 2009

(54) BEVERAGE BOTTLING PLANT FOR FILLING BOTTLES WITH A LIQUID BEVERAGE MATERIAL AND A METHOD AND DEVICE FOR THE TREATMENT OF BOTTLES AND CONTAINERS TO BE FILLED

(75) Inventor: Volker Till, Hofheim/Taunus (DE)

(73) Assignee: KHS Maschinen-Und Anlagenbau AG, Dortmund (DE)

( * ) Notice: Subject to any disclaimer, the term of this patent is extended or adjusted under 35 U.S.C. 154(b) by 598 days.

(21) Appl. No.: 11/167,077

(22) Filed: Jun. 24, 2005

(65) Prior Publication Data
US 2006/0005896 A1 Jan. 12, 2006

(30) Foreign Application Priority Data
Jun. 26, 2004 (DE) .................. 10 2004 030 957

(51) Int. Cl.
- *B67C 3/00* (2006.01)
- *B65B 31/00* (2006.01)
- *B65B 3/04* (2006.01)
- *B65B 55/24* (2006.01)
- *B65B 55/02* (2006.01)

(52) U.S. Cl. ............ 141/5; 141/11; 141/63; 141/82; 141/92; 141/144; 53/167; 53/272; 53/425; 422/28; 422/292

(58) Field of Classification Search .......... 141/5, 141/11, 63, 69, 70, 82, 89, 91, 92, 144, 145; 53/111 RC, 127, 425, 426, 167, 272; 422/28, 422/292

See application file for complete search history.

(56) References Cited

U.S. PATENT DOCUMENTS

| | | | | |
|---|---|---|---|---|
| 4,742,667 A | * | 5/1988 | Muller et al. ................. | 53/167 |
| 5,398,734 A | * | 3/1995 | Hartel ........................ | 141/82 |
| 5,713,403 A | * | 2/1998 | Clusserath et al. .......... | 141/101 |
| 6,096,265 A | * | 8/2000 | Mezger et al. ................ | 422/28 |
| 6,120,730 A | * | 9/2000 | Palaniappan et al. .......... | 422/28 |
| 6,786,249 B2 | * | 9/2004 | Armbruster et al. ........... | 141/92 |
| 7,010,900 B2 | * | 3/2006 | Grossmann et al. ........... | 53/167 |
| 7,360,345 B2 | * | 4/2008 | Topf ........................... | 53/426 |

(Continued)

FOREIGN PATENT DOCUMENTS

DE 32 35 476 A1 5/1983

(Continued)

OTHER PUBLICATIONS

European Patent Office Search Report EP 05 01 1068 and English translation thereof.

*Primary Examiner*—Timothy L Maust
*Assistant Examiner*—Nicolas A Arnett
(74) *Attorney, Agent, or Firm*—Nils H. Ljungman & Associates

(57) ABSTRACT

A container filling plant for filling containers comprising a plastic material with a filling material and a method of operation thereof. The container filling plant has at least one treatment device having a source of a treatment agent, wherein at least one pulse of the treatment agent is configured to be heated to treat the inside surface of a container without destructive effects on the container.

20 Claims, 6 Drawing Sheets

U.S. PATENT DOCUMENTS

2002/0159915 A1* 10/2002 Zelina et al. .................. 422/3
2004/0208781 A1 10/2004 Hayashi
2004/0237466 A1* 12/2004 Grossmann et al. ........... 53/167

FOREIGN PATENT DOCUMENTS

| DE | 33 39 930 A1 | 5/1985 |
| DE | 199 49 692 A1 | 4/2001 |
| WO | WO 01/28863 A1 | 4/2001 |
| WO | WO 02/064174 A | 8/2002 |
| WO | WO 03/022689 A | 3/2003 |
| WO | WO 03/030950 A | 4/2003 |

* cited by examiner

BEVERAGE BOTTLING PLANT FOR FILLING BOTTLES WITH A LIQUID BEVERAGE MATERIAL AND A METHOD AND DEVICE FOR THE TREATMENT OF BOTTLES AND CONTAINERS TO BE FILLED

BACKGROUND

1. Technical Field

The present application relates to a beverage bottling plant for filling bottles with a liquid beverage material and a method and device for the treatment of bottles and containers to be filled.

2. Background Information

A beverage bottling plant for filling bottles with a liquid beverage filling material can possibly comprise a beverage filling machine with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine. Upon filling, a closing station closes the filled bottles. There may further be provided a conveyer arrangement configured to transfer filled bottles from the filling machine to the closing station. Bottles may be labeled in a labeling station, the labeling station having a conveyer arrangement to receive bottles and to output bottles. The closing station and the labeling station may be connected by a corresponding conveyer arrangement.

In the beverage industry, for example, e.g. for the bottling of beverages in bottles or similar containers, it is frequently necessary to sterilize these containers, at least on their interior surfaces, prior to bottling to achieve the required sterility and thus the shelf life of the bottled product.

One process that is widely used is hydrogen peroxide sterilization. In these methods, liquid hydrogen peroxide, for example, is finely atomized and mixed with a current of air, whereby the air is generally a current of sterile air. Then this hydrogen peroxide-air mixture is fed to a vaporizer in which any hydrogen peroxide that is still liquid is completely vaporized. Then this mixture of vapor and air is introduced into the containers to be sterilized, where the hydrogen peroxide immediately condenses on the cold interior walls of the container, where it forms a uniform liquid film. For the subsequent activation of the hydrogen peroxide, i.e. to initiate the decomposition of the hydrogen peroxide, it is necessary to heat it to a specified temperature, or to add a specified amount of heat to it, which as a rule is transferred to the hydrogen peroxide by means of an activation medium. In most cases, this activation medium is sterile warm air that is injected into the containers and has been heated to the temperature required for the activation of the hydrogen peroxide.

During the decomposition process, the hydrogen peroxide decomposes into water and free radicals, namely atomic oxygen O and HO groups which essentially perform the actual sterilization. After the conclusion of the sterilization, the containers are blown out by means of rinsing air and/or dry air and dried.

Because the rate of decomposition of the hydrogen peroxide increases superproportionally as the activation temperature increases, as a result of which significant reductions of the cycle times can be achieved, it is theoretically desirable to work at the highest possible temperatures.

Especially with bottles or containers made of plastic, for example PET bottles or containers, an additional problem is that an overheating of these containers above a critical temperature or boundary temperature leads to the destruction or deformation of the containers, and must therefore be avoided throughout the sterilization process.

OBJECT OR OBJECTS

The object is to describe a method that makes it possible to also reliably sterilize such containers, especially those that are temperature-sensitive on account of the container material used, i.e. that may not be heated above a specified maximum working temperature, and specifically with sufficiently high capacity (number of containers processed per unit of time). The present application teaches that this object is accomplished by a method as described herein below.

SUMMARY

In the method taught by the present application, the activation medium is heated to a processing temperature that is significantly higher than the maximum working temperature of the containers to be processed. To achieve a comprehensive and rapid activation of the hydrogen peroxide, but to simultaneously avoid any damage to the containers, the hot activation medium is introduced into the individual containers during the activation phase in the form of pulses, for example all at once and/or in multiple introductions with interruptions, whereby the length of time during which the hot activation medium flows into the individual containers is then always shorter than the total duration of the activation phase.

The method taught by the present application, however, is not exclusively suitable for the hydrogen peroxide sterilization of PET or plastic bottles or similar containers, the critical maximum working temperature of which is between approximately fifty five degrees Celsius and sixty degrees Celsius, whereby the containers may not be heated above this maximum working temperature to prevent shrinkage or deformation.

In the method taught by the present application, the processing or dispensing temperature of the hot activation medium is in the range between one hundred thirty degrees Celsius and one hundred fifty degrees Celsius, for example.

The present application is based on the knowledge that the speed of activation or decomposition of the hydrogen peroxide increases exponentially with the increase in temperature or with the increase in temperature of the activation medium, while on the other hand, the introduction of heat into the containers and thus the temperature of the containers increases only in a straight line with the temperature of the activation medium.

As a result of the pulsed dispensing of the highly heated activation medium also taught by the present application, as the activation speed is further optimized, the introduction of heat into the containers is further reduced, so that the containers are not heated above their maximum working temperature.

A sterilizer for the performance of the method is described herein below.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The present application is explained in greater detail below on the basis of an exemplary embodiment which is illustrated in the accompanying drawings, in which.

DESCRIPTION OF EMBODIMENT OR EMBODIMENTS

Figure 1A:
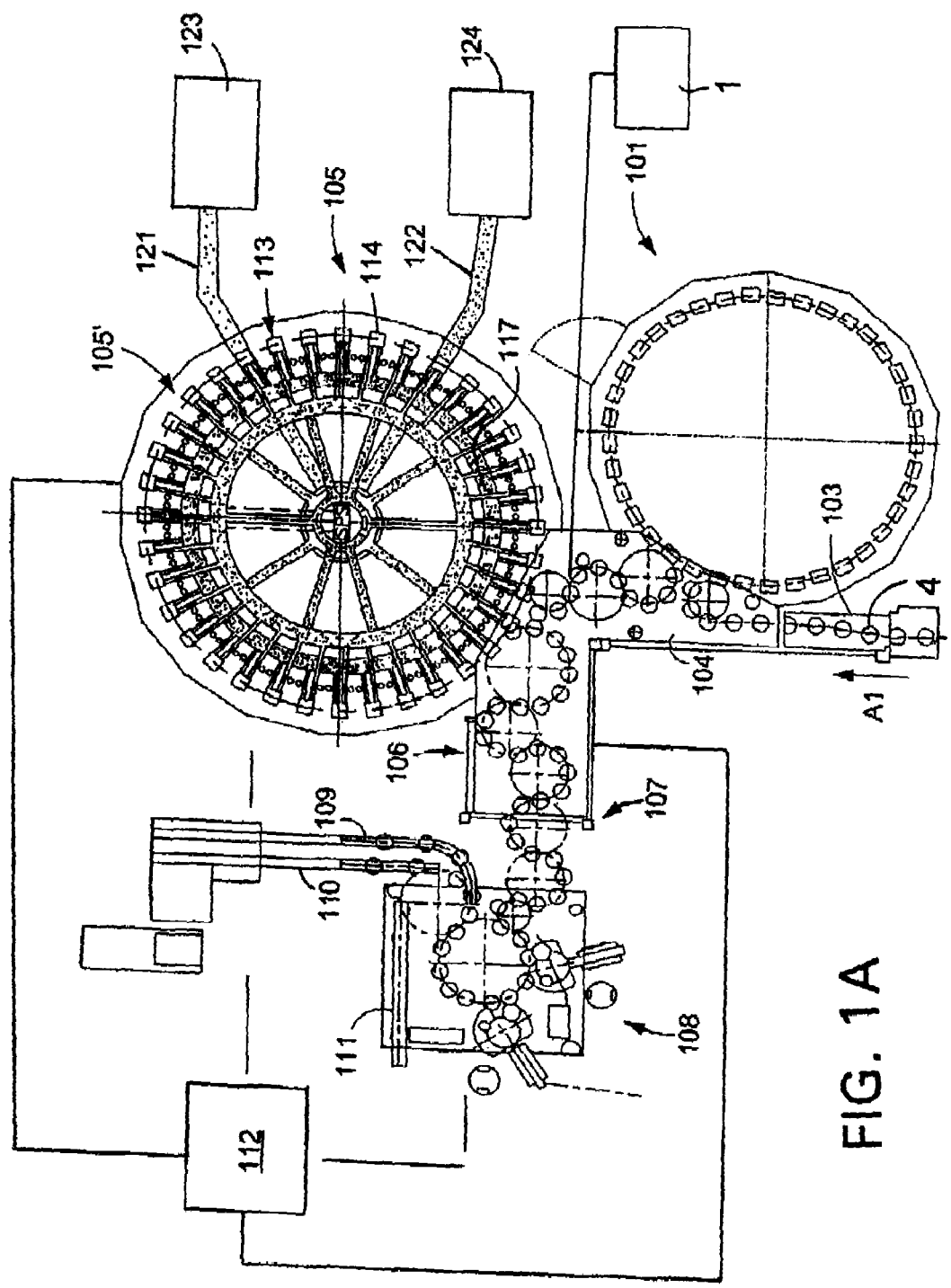
FIG. 1A is a schematic illustration of a container filling plant in accordance with one possible embodiment.
Figure 1:
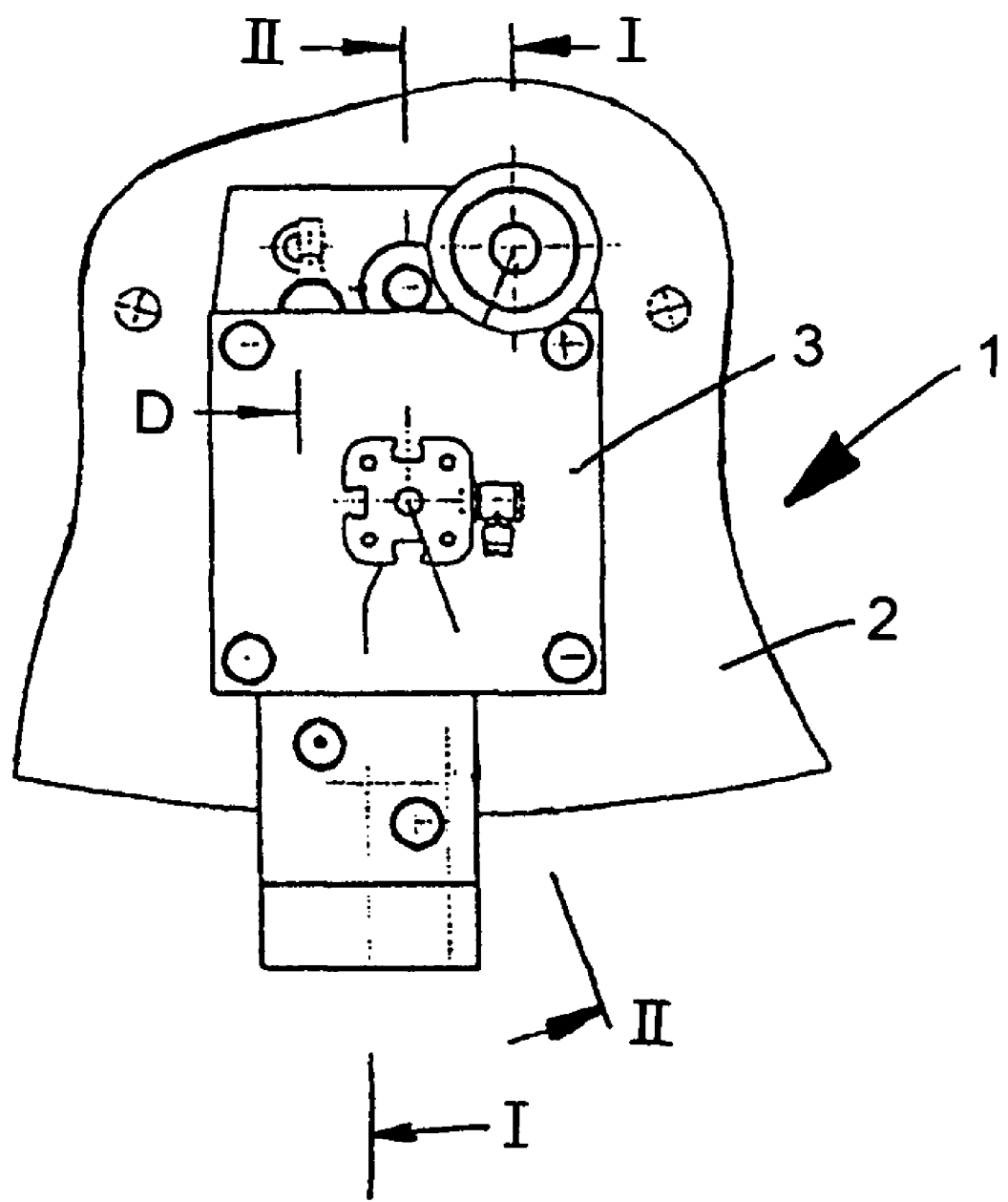
FIG. 1 is a simplified overhead view of a rotor that rotates around a vertical machine axis of a sterilizer for bottles (plastic bottles, such as PET bottles, for example), or similar containers with a sterilizer or vaporizer head provided on the periphery of this rotor.

FIG. 1A shows schematically the main components of one possible embodiment example of a system for filling containers, specifically, a beverage bottling plant for filling bottles 4 with at least one liquid beverage, in accordance with at least one possible embodiment, in which system or plant could possibly be utilized at least one aspect, or several aspects, of the embodiments disclosed herein.

FIG. 1A shows a rinsing arrangement or rinsing station 101, to which the containers, namely bottles 4, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles 4 are transported to a beverage filling machine 105 by a second conveyer arrangement 104 that is formed, for example, by one or more starwheels that introduce bottles 4 into the beverage filling machine 105.

The beverage filling machine 105 shown is of a revolving or rotary design, with a rotor 105', which revolves around a central, vertical machine axis. The rotor 105' is designed to receive and hold the bottles 4 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 4 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles 4, there can be a beverage bottle closing arrangement or closing station 106 which closes or caps the bottles 4. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 4. In the embodiment shown, the labeling arrangement 108 has three output conveyer arrangement: a first output conveyer arrangement 109, a second output conveyer arrangement 110, and a third output conveyer arrangement 111, all of which convey filled, closed, and labeled bottles 4 to different locations.

The first output conveyer arrangement 109, in the embodiment shown, is designed to convey bottles 4 that are filled with a first type of liquid beverage supplied by, for example, the supply reservoir 123. The second output conveyer arrangement 110, in the embodiment shown, is designed to convey bottles 4 that are filled with a second type of liquid beverage supplied by, for example, the supply reservoir 124. The third output conveyer arrangement 111, in the embodiment shown, is designed to convey incorrectly labeled bottles 4. To further explain, the labeling arrangement 108 can comprise at least one beverage bottle inspection or monitoring device that inspects or monitors the location of labels on the bottles 4 to determine if the labels have been correctly placed or aligned on the bottles 4. The third output conveyer arrangement 111 removes any bottles 4 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

FIG. 1A further shows a treatment or sterilization device 1, which treatment or sterilization device 1 is disposed between the beverage bottle cleaning machine and the beverage bottle filling machine.

The sterilizer, which is designated 1 in general in the accompanying figures, and of which only a driven rotor 2 that rotates around a vertical machine axis and a sterilizer head 3 are shown, is used for the sterilization (hydrogen peroxide sterilization) of temperature-sensitive containers, namely PET bottles 4 with a hot sterilization medium which is formed from an air-water aerosol by heating.

In the drawings, reference numeral 1 refers to a sterilizer; reference numeral 2 refers to a rotor; reference numeral 2.1 refers to a bottle carrier; reference numeral 3 refers to a sterilizer head; reference numeral 4 refers to PET bottles; reference numeral 5 refers to head exchangers; reference numeral 6 refers to a housing; reference numeral 7 refers to a flow channel; reference numeral 8 refers to a core; reference numeral 9 refers to a device; reference numeral 10 refers to a connection; reference numeral 11 refers to a nozzle; reference numeral 12 refers to a connection; reference numeral 13 refers to a heater device; reference numeral 14 refers to a closure element; reference numeral 15 refers to a guide channel; reference numeral 16 refers to a rod; reference numeral 17 refers to an actuator device; reference numeral 18 refers to restoring spring; reference numeral 19 refers to a boring; reference numerals 20, 21, and 22 refer to gasket; reference numeral 23 refers to a chamber; reference numeral 24 refers to a boring; reference numeral 25 refers to a control opening; reference numeral 26 refers to a tube; reference numeral 27 refers to a dispensing opening; reference numeral 28 refers to a control valve; reference letters KA refer to treatment device head axis.

Provided underneath each of the sterilizer heads 3, which are located, for example, at uniform angular intervals on the periphery of the rotor 2, is a container or bottle carrier 2.1, in which the individual bottle to be sterilized is suspended, for example, and namely so that it is equi-axial with a vertical sterilizer head axis KA, so that when the sterilizer head 3 is activated, a stream of hot sterilization medium can be dispensed into the interior of the bottle 4 to be sterilized, which is located underneath the sterilization head 3.

The sterilizer head 3 comprises a heater or heat exchanger 5 with a housing 6 in which, among other things, a flow channel or heating channel 7 is realized that surrounds the axis KA in a helical fashion, and namely in the illustrated embodiment so that a core 8 is inserted in a cylindrical opening of the housing 6, which opening is coaxial with the axis KA, and which core has a helical groove on its periphery that forms the flow channel 7.

Figure 2:
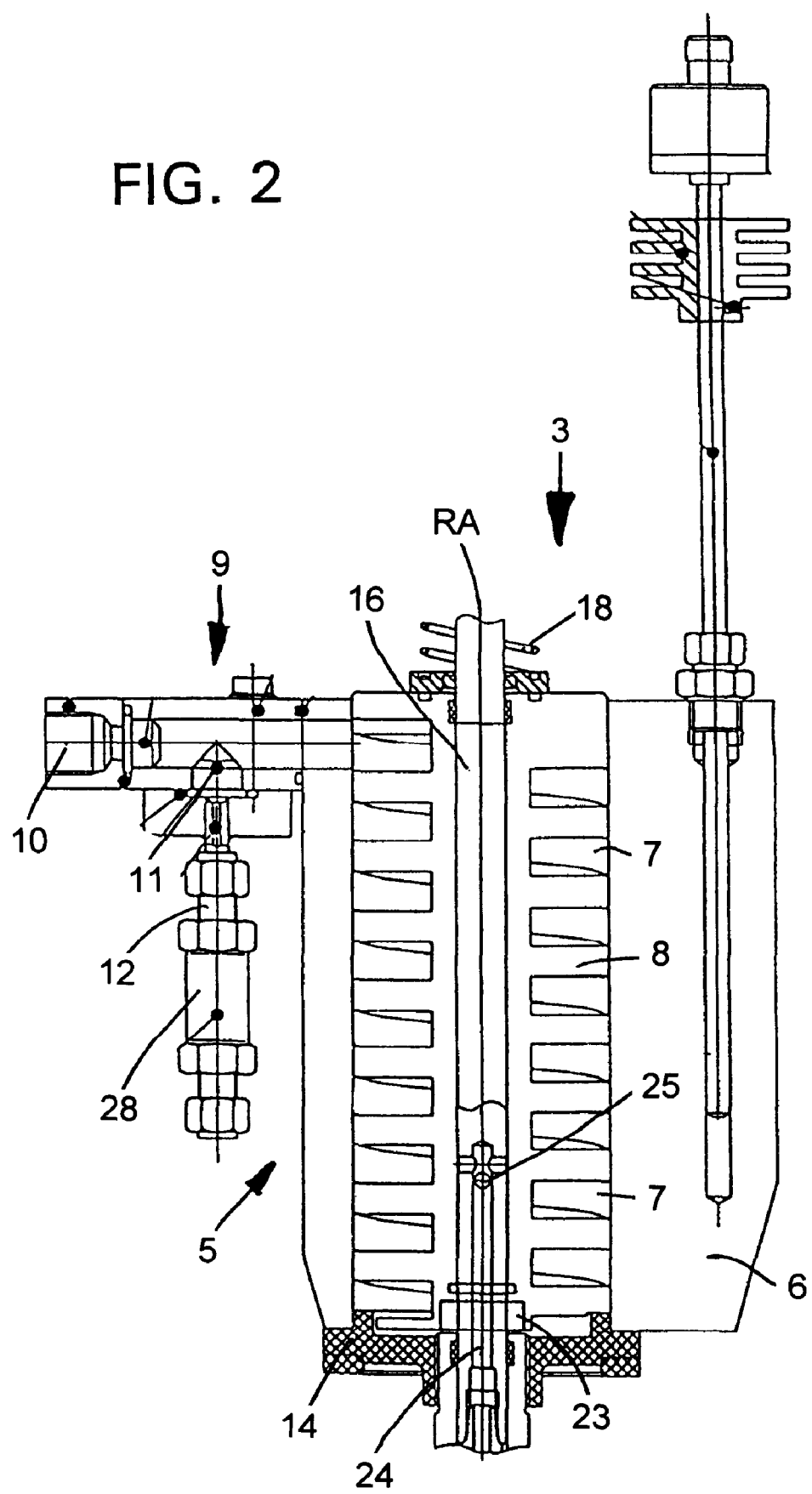
FIGS. 2 and 3 are sectional view along Lines I-I and II-II respectively in FIG. 1.
Figure 3:
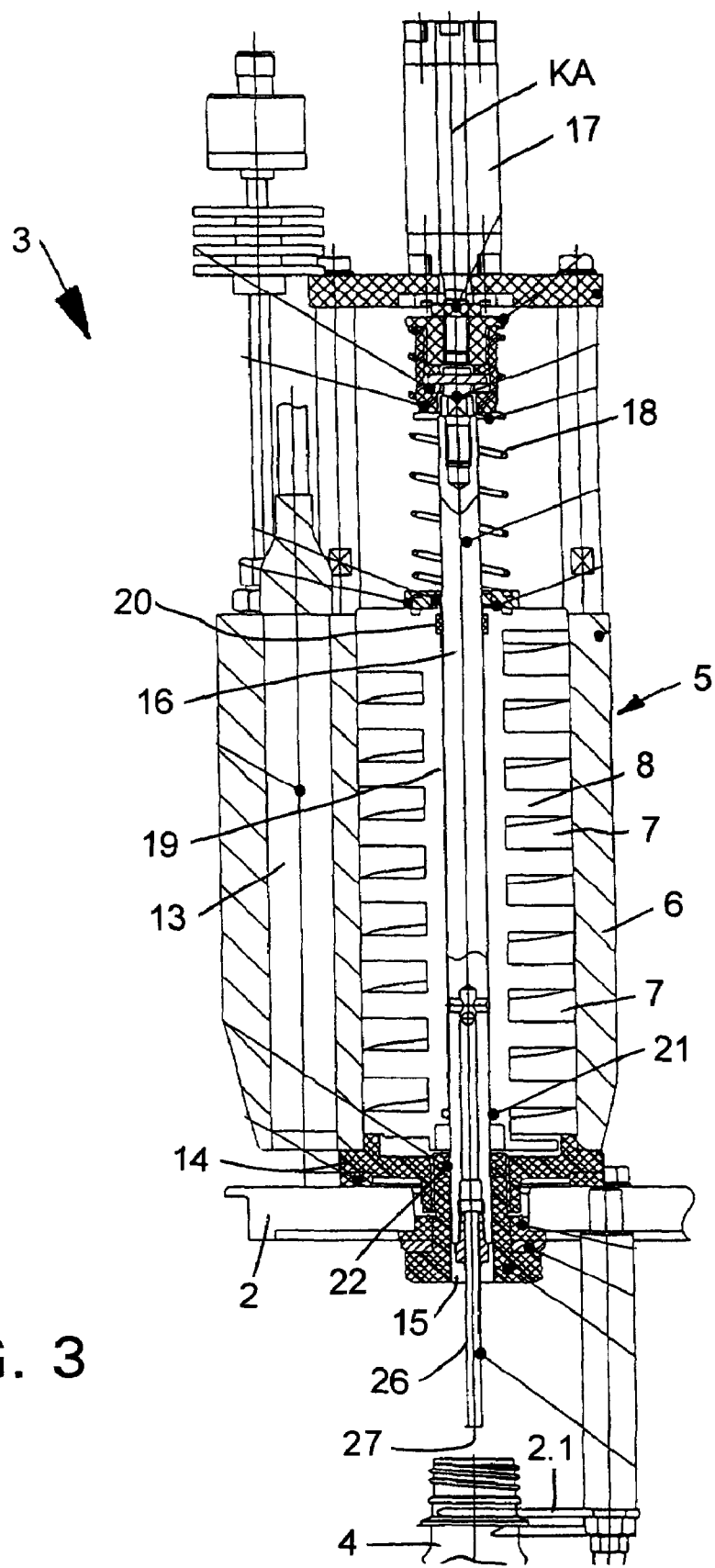

The upper end of the flow channel 7 shown in FIGS. 2 and 3, which is closed toward the outside, is in communication with a sprayer device 9 which supplies sterile compressed air via the connection 10 and which has a spray nozzle 11 which is supplied with hydrogen peroxide by means of the connection 12 and a pump (not shown), e.g. a membrane pump, which is connected with this connection, whereby the hydrogen peroxide is then introduced to form the hydrogen peroxide-air aerosol via the spray nozzle 11 in the form of a finely sprayed jet or mist into the air flow that is flowing through the spray device 9, so that this aerosol which comprises air and hydrogen peroxide then arrives in the flow channel 7 of the heat exchanger 5.

By means of a heating device, which in the illustrated exemplary embodiment is formed by an electrical heating cartridge with a thermo-sensor, the heat exchanger 5 and in particular also the core 8 is heated, and specifically to a temperature that is significantly above the maximum working temperature to which the bottles 4 may be heated without damage or deformation. With the heating element 13, the core 8 is heated, for example, to a temperature in the range between approximately one hundred thirty degrees Celsius and one hundred fifty degrees Celsius.

The lower end of the housing 6 is formed by a closing element 14, by means of which the respective sterilizer head 3 in the illustrated exemplary embodiment is also fastened to the rotor 2, and in which a guide channel 15 for a rod 16 is realized equi-axially with the axis KA and open on the underside of the closing element 14. This guide channel 15 defines, with its axis, the axis KA and can be moved downward in the direction of the axis AK into an operating position by an actuator device 17, which is provided above the heat exchanger 5, from the raised idle position illustrated in FIGS. 2 and 3, against the action of a restoring spring 18.

The rod 16 is also guided in a boring 19 which is realized equi-axially with the axis KA in the core 8, and is also sealed in the vicinity of the upper side of the core 8 by gaskets 20 and in the lower portion of the core 8 by a seal 21 formed by an O-ring. By means of an additional seal 22, which in the illustrated exemplary embodiment is also formed by an O-ring, the rod is guided in the opening 16 in a sealed manner. In the lower portion, the core 8 forms a chamber 23 that surrounds the rod 16, which chamber is in communication with the lower end of the flow channel 7.

In the lower portion of the rod 16, a channel 24 that is coaxial with the axis of this rod and is open on the underside of the rod, which channel 24 is open on its upper end by means of control openings 25 formed by transverse borings on the periphery of the rod 16. In the position illustrated in FIGS. 2 and 3, the control openings 25 are located inside the boring 19, so that there is no flow connection out of the chamber 23 via the control openings 25 into the channel 24. If the rod 16 is moved downward by the actuator device 17 into its activated or operating position, the control openings 25 are located in the chamber 23, as a result of which there is a flow connection from this chamber via the control openings 25 into the channel 24.

On the lower end of the rod 16, a tube 26 is fastened so that it can be exchanged or replaced, and so that said tube 26 is co-axial with the axis of the rod 16 and projects beyond the underside of the sterilizer head 3 or of the closure element 14. After the tube 26 is fastened, the channel realized in the tube is connected with the channel 24.

For the sterilization of the bottles 4, first the heat exchangers 5 of the heat exchanger heads 3 are heated by means of their electric heater devices 13 to the required processing temperature, for example to a temperature between one hundred thirty degrees Celsius and one hundred fifty degrees Celsius.

The bottles to be sterilized are then transferred individually to a bottle receptacle on a bottle holder 2.1 of the rotating rotor 2 and after sterilization are removed from the rotor on a bottle outlet or are transported onward to a downstream filling machine. During the rotary movement of the rotor 2 between the bottle inlet and bottle outlet, the respective actuator device 17 is actuated in a controlled manner, so that the rod 16 and with it also the respective tube 26 are introduced into the bottle 4, so that by means of the channel 24 that is in communication with the chamber 23 via the openings 25 and the tube channel realized in the tube 26, the heated sterilization medium that is produced in the spray device 9 and is heated as it flows through the helical or spiral flow channel 7, and which comprises hot air and in particular of vaporized hydrogen peroxide, is introduced into the respective bottle 4 via the dispensing opening 27 that is formed on the lower end of the tube 26.

Because a relatively high operating temperature (in the range of approximately one hundred thirty degrees Celsius and one hundred fifty degrees Celsius) is selected for the respective heat exchanger 5, it is possible to keep the proportion of hydrogen peroxide which is introduced into the air stream via the spray device 9, and thus also the amount of hot sterilization medium, i.e. air and hydrogen peroxide vapor, that is introduced into the respective bottle 4 per unit of time relatively high.

To prevent damage to the bottles 4 and to still introduce the quantity of high-temperature heat into the bottles 4 that is necessary for an optimal activation of the hydrogen peroxide, during the activation process a pulsed dispensing of the hot activation medium, for which purpose a corresponding pulsed activation of the actuator device 17 is effected, for example, by moving the respective rod 16 multiple times between its idle position and its activated position. Because the air continues to be fed under pressure via the connection 10, and an elevated pressure builds up in the flow channel 7, in particular when the sterilizer head is not activated, i.e. whenever the rod 16 is in its idle position, it is possible to achieve an elevated enthalpy or quantity of heat, but in particular an elevated temperature for the hot activation medium.

After the sterilization, the bottle 4 is blown out to remove condensate or remaining water. 28 is a control valve in the supply line of the spray nozzle 11, with which the hydrogen peroxide supply to this nozzle can be interrupted.

The present application was described above with reference to one exemplary embodiment. It goes without saying that numerous modifications and variants are possible without thereby going beyond the scope of the teaching of the present application. In the above description, for example, the heat exchanger 5 is heated by means of the electric heater device 13 (heater cartridge with temperature sensor), although there are other possibilities, such as heating by means of steam, for example.

Figure 4:
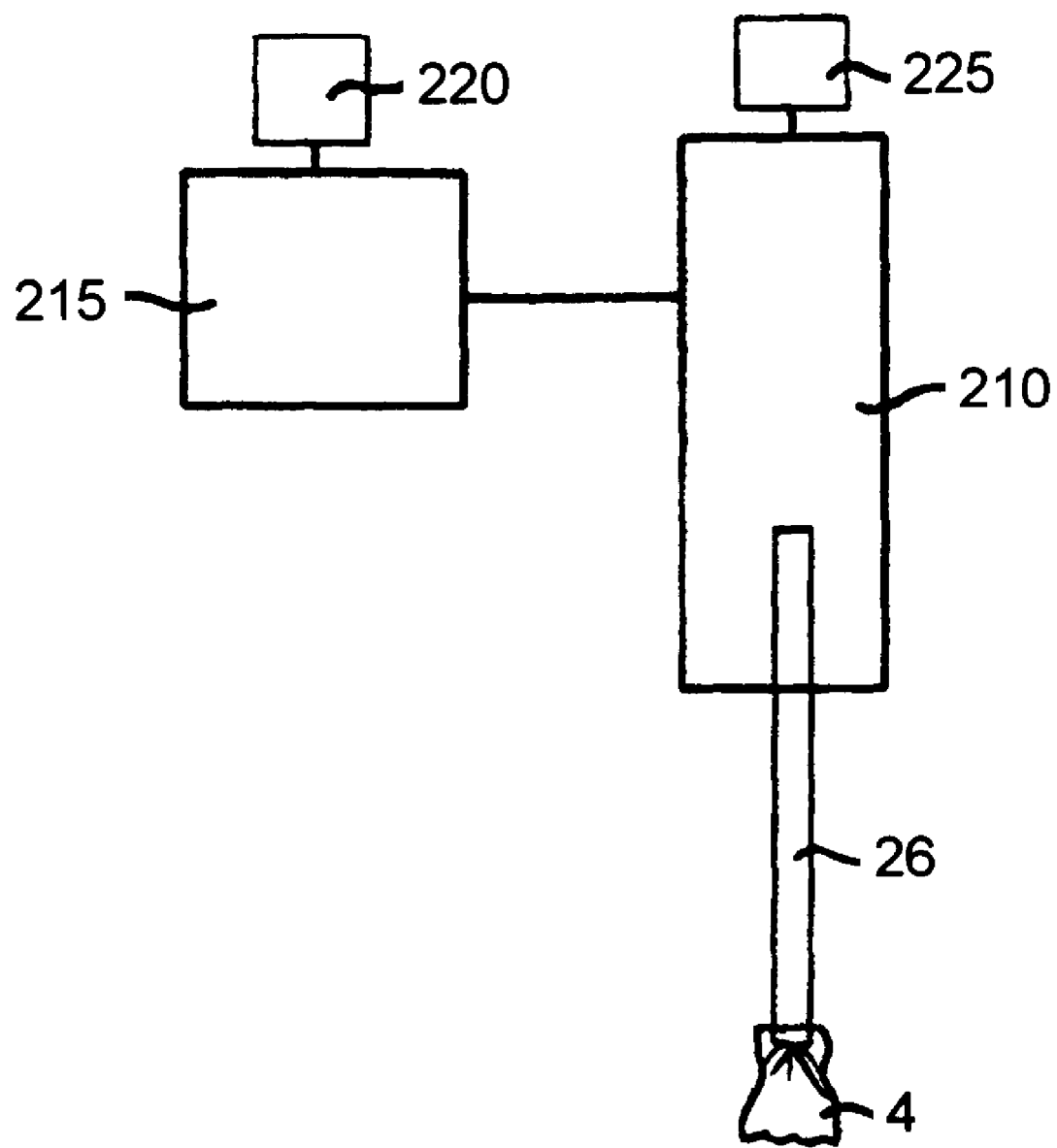
FIG. 4 is a box drawing of one possible embodiment of a treatment device.

FIG. 4 shows a box diagram of a treatment device according to one possible embodiment. In this possible embodiment, a pulse injecting system 210 could be driven by a pump 215. The pump 215 could comprise a cam structure 220, and the pulse injecting system 210 could comprise a cam structure 225. The pump 215 could drive the injection system to move the tube 26 into an engaged position, and into a disengaged position. In the engaged position, treated air is pulsed into a bottle 4. The tube could then be moved into a disengaged position, then back into an engaged position, in a pulsing manner. In another possible embodiment, the tube 26 could inject treated air into a bottle 4 while being pushed into an engaged position, and while being pulled into a disengaged position.

Figure 5:
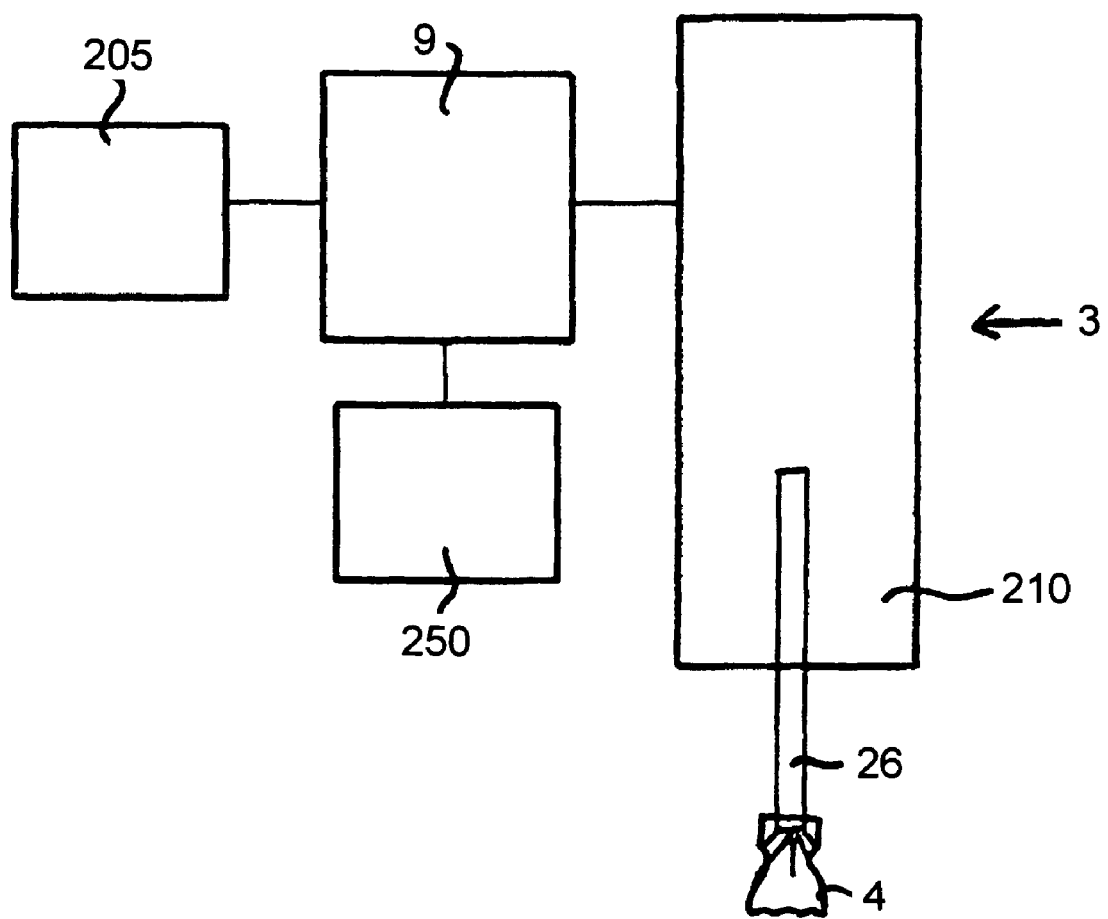
FIG. 5 is a box drawing of another possible embodiment of a treatment device.

According to FIG. 5, another possible embodiment of a treatment device could comprise a supply of air 205 and a supply of treatment agent 250. The treatment agent could possibly be hydrogen peroxide, nitrogen, or any number of different treatment agents. Air could flow from the supply of air 205 and treatment agent could flow from the supply of treatment agent into the spraying device 9, where air and treatment agent are mixed to form treated air to treat bottles. Treated air then flows into the heat exchanger head 3 to be heated. Once treated air is heated, it flows into the pulse injecting system 210 to be pulsed into bottles. The pulse injecting system 210 permits heated, treated air to be pulsed into bottles 4 via the tube 26 in a controlled, pulsed manner.

In one possible embodiment, the pulsed opening and closing of the valve system could be designed to heat only the inner surface of the bottle that is being treated, so as not to contort the bottle with excessive heat. In another possible embodiment, the pulsed opening and closing of the valve system could last milliseconds, such that bottles may be moved through the treatment machine at a high rate. However, in other possible embodiments, the pulsed opening and closing of the valve system could last longer or shorter than a few milliseconds.

Depending upon the material of which bottles are made, the thickness of the bottles, or the size and shape of the bottles, the length of the pulse of treatment material into the bottles may be shorter or longer in other possible embodiments to accommodate different bottles. Further, the amount of treatment material dispensed into the bottles may be lesser or greater in other possible embodiments depending on different types of bottles. The amount of treatment material pulsed into bottles and the length of the pulse and the time between pulses in different embodiments may be determined through experimentation.

An example of a treatment device for treating bottles to be filled which may possibly be utilized or adapted for use in at least one possible embodiment may possibly be found in German Application number 10 2004 029 803.3, filed on Jun. 19, 2004, having inventor Thomas Stienen, and U.S. patent application entitled "A beverage bottling plant for filling bottles with a liquid beverage material having a treatment device for the treatment of bottles", having inventor Thomas Stienen, filed on Jun. 17, 2005. The above application is hereby included by reference as if set forth in its entirety herein.

One feature or aspect of an embodiment is believed at the time of the filing of this patent application to possibly reside broadly in a sterilization method, in particular for the sterilization of bottles or similar containers, in particular of temperature-sensitive containers such as PET bottles, for example, whereby the hydrogen peroxide introduced into the container is activated by an activation medium, characterized by the fact that the activation medium is heated to a temperature that is above a maximum working temperature of the containers, and that the hot activation medium is introduced into the respective containers in a pulsed manner.

Another feature or aspect of an embodiment is believed at the time of the filing of this patent application to possibly reside broadly in a method as claimed in Claim 1, characterized by the fact that the containers are PET bottles.

Yet another feature or aspect of an embodiment is believed at the time of the filing of this patent application to possibly reside broadly in a sterilization method, characterized by the fact that the activation medium is heated to a temperature in the range between approximately one hundred thirty degrees Celsius to one hundred fifty degrees Celsius.

Still another feature or aspect of an embodiment is believed at the time of the filing of this patent application to possibly reside broadly in a sterilization method, characterized by the fact that during the processing, the introduction of the hot activation medium is interrupted at least once.

A further feature or aspect of an embodiment is believed at the time of the filing of this patent application to possibly reside broadly in a sterilization method, characterized by the fact that the hot activation medium is introduced into the individual bottle by a tube that is introduced into the bottle.

Another feature or aspect of an embodiment is believed at the time of the filing of this patent application to possibly reside broadly in a sterilization method, characterized by the use of a sterilizer with at least one sterilizer head and at least one heat exchanger in which an activation medium is heated to a temperature that is above the maximum working temperature of the container and is introduced by means of an outlet in a pulsed manner into the interior of the container to be sterilized.

Yet another feature or aspect of an embodiment is believed at the time of the filing of this patent application to possibly reside broadly in a sterilizer for the processing, in particular for the hydrogen peroxide sterilization of bottles or similar containers, whereby the hydrogen peroxide introduced into the containers is activated by an activation medium, with at least one heater channel through which the activation medium flows to heat the activation medium to a processing temperature, and with a valve control for the timed dispensing of the hot activation medium via a dispensing opening into the interior of the container to be sterilized, whereby the valve control has a control valve system and an actuator device which are realized so that they effect a pulsed opening and closing of the valve system.

Still another feature or aspect of an embodiment is believed at the time of the filing of this patent application to possibly reside broadly in a sterilizer, characterized in that the heater channel is realized to heat the activation medium to a processing temperature in the range between approximately one hundred thirty degrees Celsius and one hundred fifty degrees Celsius.

A further feature or aspect of an embodiment is believed at the time of the filing of this patent application to possibly reside broadly in a sterilizer, characterized by the fact that the heater channel is a channel that is coiled around an axis of the sterilizer head.

Another feature or aspect of an embodiment is believed at the time of the filing of this patent application to possibly reside broadly in a sterilizer, characterized by the fact that the heater channel is realized in a housing of a heat exchanger of the sterilizer head.

Yet another feature or aspect of an embodiment is believed at the time of the filing of this patent application to possibly reside broadly in a sterilizer, characterized by the fact that in the housing, a core is held, which has at least one groove on its periphery that forms the heater channel.

Still another feature or aspect of an embodiment is believed at the time of the filing of this patent application to possibly reside broadly in a sterilizer, characterized by a rod that can be moved axially by the actuator device in an axis parallel to a vertical sterilizer axis between an idle position and a work position, in which rod an axial channel is formed that is in communication with the dispensing opening, and which has, on the end the is farther from the dispensing opening, at least one control opening, which when the rod is in the work position is in communication with the heater channel or with a chamber that is connected with said channel.

A further feature or aspect of an embodiment is believed at the time of the filing of this patent application to possibly reside broadly in a sterilizer, characterized by the fact that the tube that forms the dispensing opening can be fastened on the end farther from the discharge openings to one end of the rod, preferably so that it can be replaced or exchanged.

Another feature or aspect of an embodiment is believed at the time of the filing of this patent application to possibly reside broadly in a sterilizer, characterized by the fact that preceding the heater channel in the direction of flow there is a sprayer device for the introduction of the water by means of at least one spray nozzle.

Yet another feature or aspect of an embodiment is believed at the time of the filing of this patent application to possibly reside broadly in a sterilizer, characterized by a heater device, for example an electrical heater device or heater cartridge, to heat the heater channel.

Still another feature or aspect of an embodiment is believed at the time of the filing of this patent application to possibly reside broadly in a sterilizer, characterized by a plurality of sterilizer heads on the periphery of a rotor that rotates around a vertical machine axis.

A further feature or aspect of an embodiment is believed at the time of the filing of this patent application to possibly reside broadly in a beverage bottling plant for filling beverage bottles with liquid beverage material, said beverage bottling plant comprising: a beverage bottle cleaning machine being configured and disposed to clean beverage bottles; a feed arrangement to supply beverage bottles to said beverage bottle cleaning machine; a beverage filling machine being configured and disposed to fill beverage bottles with liquid beverage material; said beverage filling machine comprising a plurality of beverage filling elements for filling beverage bottles with liquid beverage material; at least one liquid reservoir being configured to hold a liquid to be bottled; said at least one liquid reservoir comprising a gas headspace being disposed above a liquid to be bottled within said at least one liquid reservoir; at least one supply line being configured and disposed to connect said at least one liquid reservoir to said beverage filling machine to supply liquid beverage material to said beverage filling machine; a first conveyer arrangement being configured and disposed to move beverage bottles from said beverage bottle cleaning machine into said beverage filling machine; said first conveyer arrangement comprising a star wheel structure; a beverage bottle closing machine being configured and disposed to close tops of filled beverage bottles; a second conveyer arrangement being configured and disposed to move filled beverage bottles from said beverage filling machine into said beverage bottle closing machine; said second conveyer arrangement comprising a star wheel structure; a beverage bottle labeling machine being configured and disposed to label filled, closed beverage bottles; a third conveyor arrangement being configured and disposed to move filled, closed beverage bottles from said beverage bottle closing machine into said beverage bottle labeling machine; said third conveyer arrangement comprising a star wheel structure; a beverage bottle packing station being configured and disposed to package labeled, filled, closed beverage bottles; a fourth conveyer arrangement being configured and disposed to move labeled, filled, closed beverage bottles from said beverage bottle labeling machine to said beverage bottle packing station; said fourth conveyer arrangement comprising a linear conveyor structure being configured and disposed to arrange beverage bottles in groups for packing; a computer control system being configured and disposed to monitor and control operation of said beverage bottling plant; a beverage bottle treatment machine being configured and disposed to treat bottles to be filled; said beverage bottle treatment machine comprising: a treatment device being configured and disposed to treat the insides of bottles to be filled, comprising: a supply for containing treatment agent to treat bottles; a spray device being configured and disposed to introduce compressed air into said treatment device and to mix said compressed air with a supply of treatment agent to create treated air to treat bottles; a heater or heat exchanger being configured and disposed to heat treated air; a helical heating channel being configured and disposed to heat treated air and to permit the flow of treated air; a vertical tube being configured and disposed to permit the flow of treated air into a bottle; said tube comprising a dispensing opening being configured and disposed to permit the flow of treated air into a bottle; said helical heating channel being disposed about said tube; a rod being disposed vertically and being configured and disposed to move up and down from an engaged position to a disengaged position, and from a disengaged position to an engaged position; said rod comprising a channel being in connection with said dispensing opening; an actuator device being configured and disposed to move said rod from an engaged position to a disengaged position, and from a disengaged position to an engaged position; a control valve system being configured and disposed to inject at least one pulse of treated air into a bottle; a pumping arrangement being configured and disposed to pump treated air into a bottle to be treated; said pumping arrangement being configured to pump and inject at least one pulse of agent into a container, which pulse of agent is so short that the heated agent does not have destructive effects on the container. a housing being configured and disposed to house said treatment device.

A further feature or aspect of an embodiment is believed at the time of the filing of this patent application to possibly reside broadly in: In a container filling plant, a device to treat a container comprising: a source of a treatment agent; an apparatus being configured and disposed to treat gas with treatment agent; a heater being configured and disposed to heat treated gas prior to entry into a container; said heater being configured to heat treated gas to a temperature greater than the temperature which a container can tolerate without destructive effects on the container; a pumping arrangement being configured to pump and inject at least one pulse of heated gas into a container, which pulse of heated gas is so short that the heated gas does not have destructive effects on the container.

Some examples of pulsing pumps or fuel injectors which may possibly be utilized or adapted for use in at least one possible embodiment may possibly be found in the following U.S. Pat. No. 6,634,325, entitled "Fuel injection system for linear engines;" U.S. Pat. No. 6,237,567, entitled "Fuel-injection system for engine;" U.S. Pat. No. 6,059,204, entitled "Accumulator injection system;" U.S. Pat. No. 6,053,150, entitled "Fuel-injection system for engines;" U.S. Pat. No. 5,443,047, entitled "Fuel injection system;" and U.S. Pat. No. 5,349,811, entitled "Pulsed fuel injection system for reducing $NO_x$ emissions."

Some examples of bottling systems, which may be used or adapted for use in at least one possible embodiment of the present may be found in the following U.S. patents assigned to the Assignee herein, namely: U.S. Pat. No. 4,911,285; U.S. Pat. No. 4,944,830; U.S. Pat. No. 4,950,350; U.S. Pat. No. 4,976,803; U.S. Pat. No. 4,981,547; U.S. Pat. No. 5,004,518; U.S. Pat. No. 5,017,261; U.S. Pat. No. 5,062,917; U.S. Pat. No. 5,062,918; U.S. Pat. No. 5,075,123; U.S. Pat. No. 5,078,826; U.S. Pat. No. 5,087,317; U.S. Pat. No. 5,110,402; U.S. Pat. No. 5,129,984; U.S. Pat. No. 5,167,755; U.S. Pat. No. 5,174,851; U.S. Pat. No. 5,185,053; U.S. Pat. No. 5,217,538; U.S. Pat. No. 5,227,005; U.S. Pat. No. 5,413,153; U.S. Pat. No. 5,558,138; U.S. Pat. No. 5,634,500; U.S. Pat. No. 5,713,403; U.S. Pat. No. 6,276,113; U.S. Pat. No. 6,213,169; U.S. Pat. No. 6,189,578; U.S. Pat. No. 6,192,946; U.S. Pat. No. 6,374,575; U.S. Pat. No. 6,365,054; U.S. Pat. No. 6,619,016; U.S. Pat. No. 6,474,368; U.S. Pat. No. 6,494,238; U.S. Pat. No. 6,470,922; and U.S. Pat. No. 6,463,964.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of stepping motors that may possibly be utilized or possibly adapted for use in at least one possible embodiment of the present application may possibly be found in the following U.S. patents: U.S. Pat. No. 6,348,774 issued to Andersen et al. on Feb. 19, 2002; U.S. Pat. No. 6,373,209 issued to Gerber et al. on Apr. 16, 2002; U.S. Pat. No. 6,424,061 issued to Fukuda et al. on Jul. 23, 2002; U.S. Pat. No. 6,509,663 issued to Aoun on Jan. 21, 2003; U.S. Pat. No. 6,548,923 to Ohnishi et al. on Apr. 15, 2003; and U.S. Pat. No. 6,661,193 issued to Tsai on Dec. 9, 2003.

The appended drawings in their entirety, including all dimensions, proportions and/or shapes in at least one embodiment of the invention, are accurate and are hereby included by reference into this specification.

Some examples of servo-motors that may possibly be utilized or possibly adapted for use in at least one possible embodiment of the present application may possibly be found in the following U.S. patents: U.S. Pat. No. 4,050,434 issued to Zbikowski et al. on Sep. 27, 1977; U.S. Pat. No. 4,365,538 issued to Andoh on Dec. 28, 1982; U.S. Pat. No. 4,550,626 issued to Brouter on Nov. 5, 1985; U.S. Pat. No. 4,760,699 issued to Jacobsen et al. on Aug. 2, 1988; U.S. Pat. No. 5,076,568 issued to de Jong et al. on Dec. 31, 1991; and U.S. Pat. No. 6,025 issued to Yasui on Feb. 15, 2000.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of computer systems that may possibly be utilized or possibly adapted for use in at least one possible embodiment of the present application may possibly be found in the following U.S. patents: U.S. Pat. No. 5,416,480 issued to Roach et al. on May 16, 1995; U.S. Pat. No. 5,479,355 issued to Hyduke on Dec. 26, 1995; U.S. Pat. No. 5,481,730 issued to Brown et al. on Jan. 2, 1996; U.S. Pat. No. 5,805,094 issued to Roach et al. on Sep. 8, 1998; U.S. Pat. No. 5,881,227 issued to Atkinson et al. on Mar. 9, 1999; and U.S. Pat No. 6,072,462 issued to Moshovich on Jun. 6, 2000.

All, or substantially all, of the components and methods of the various embodiments may be used with at least one embodiment or all of the embodiments, if more than one embodiment is described herein.

Some examples of control valve apparatus that may possibly be utilized or possibly adapted for use in at least one possible embodiment of the present application may possibly be found in the following U.S. patents: U.S. Pat. No. 5,406,975 issued to Nakamichi et al. on Apr. 18, 1995; U.S. Pat. No. 5,503,184 issued to Reinartz et al. on Apr. 2, 1996; U.S. Pat. No. 5,706,849 issued to Uchida et al. on Jan. 13, 1998; U.S.

Pat. No. 5,975,115 issued to Schwegler et al. on Nov. 2, 1999; U.S. Pat. No. 6,142,445 issued to Kawaguchi et al. on Nov. 7, 2000; and U.S. Pat. No. 6,145,538 issued to Park on Nov. 14, 2000.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of pneumatic arrangements that may possibly be utilized or possibly adapted for use in at least one possible embodiment of the present application may possibly be found in the following U.S. patents: U.S. Pat. No. 6,609,767 issued to Mortenson et al. on Aug. 26, 2003; U.S. Pat. No. 6,632,072 issued to Lipscomb et al. on Oct. 14, 2003; U.S. Pat. No. 6,637,838 issued to Watanabe on Oct. 28, 2003; U.S. Pat. No. 6,659,693 issued to Perkins et al. on Dec. 9, 2003; U.S. Pat. No. 6,668,848 issued to Ladler et al. on Dec. 30, 2003; and U.S. Pat. No. 6,676,229 issued to Marra et al. on Jan. 13, 2004.

All of the patents, patent applications and publications recited herein, and in the Declaration attached hereto, are hereby incorporated by reference as if set forth in their entirety herein.

Some examples of seal arrangements that may possibly be utilized or possibly adapted for use in at least one possible embodiment of the present application may possibly be found in the following U.S. patents: U.S. Pat. No. 5,411,273 issued to Pietsch et al. on May 2, 1995; U.S. Pat. No. 6,290,234 issued to Berle et al. on Sep. 18, 2001; U.S. Pat. No. 6,474,653 issued to Hintenlang et al. on Nov. 5, 2002; U.S. Pat. No. 6,616,146 issued to Friend et al. on Sep. 9, 2003; U.S. Pat. No. 6,692,007 issued to Oldenburg on Feb. 17, 2004; and U.S. Pat. No. 6,648,335 issued to Ezell on Nov. 18, 2003.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

Some examples of apparatus and methods of sterilizing or cleaning containers that may possibly be utilized or possibly adapted for use in at least one possible embodiment of the present application may possibly be found in the following U.S. patents: U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

Some examples of sterilizing or cleaning agents and concentrations thereof that may possibly be utilized or possibly adapted for use in at least one possible embodiment of the present application may possibly be found in the following U.S. patents: U.S. Pat. No. 6,039,922 issued to Swank et al. on Mar. 21, 2000; U.S. Pat. No. 6,244,275 issued to Ziegler et al. on Jun. 12, 2001; U.S. Pat. No. 6,406,666 issued to Cicla et al. on Jun. 18, 2002; and U.S. Pat. No. 6,612,149 issued to Wang et al. on Sep. 2, 2003.

The corresponding foreign patent publication applications, namely, Federal Republic of Germany Patent Application No. 10 2004 030 957.4, filed on Jun. 26, 2004, having inventor Volker Till, and DE-OS 10 2004 030 957.4, and DE-PS 10 2004 030 957.4, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

Some examples of heater arrangements that may possibly be utilized or possibly adapted for use in at least one possible embodiment of the present application may possibly be found in the following U.S. patents; U.S. Pat. No. 6,404,421 issued to Meijler et al. on Jun. 11, 2002; U.S. Pat. No. 6,515,264 issued to Toya et al. on Feb. 4, 2003; U.S. Pat. No. 6,548,786 issued to Takizawa et al. on Apr. 15, 2003; U.S. Pat. No. 6,555,796 issued to Cusack on Apr. 29, 2003; U.S. Pat. No. 6,633,727 issued to Henrie et al. on Oct. 14, 2003; and U.S. Pat. No. 6,677,557 issued to Ito et al. on Jan. 13, 2004.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

Some examples of bottling systems which may possibly be utilized or adapted for use in at least one possible embodiment may possibly be found in the following U.S. patents: U.S. Pat. No. 6,684,602, entitled "Compact bottling machine;" U.S. Pat. No. 6,470,922, entitled "Bottling plant for bottling carbonated beverages;" U.S. Pat. No. 6,390,150, entitled "Drive for bottling machine;" U.S. Pat. No. 6,374,575, entitled "Bottling plant and method of operating a bottling plant;" U.S. Pat. No. 6,192,946, entitled "Bottling system;" U.S. Pat. No. 6,185,910, entitled "Method and an apparatus for high-purity bottling of beverages;" U.S. Pat. No. 6,058,985, entitled "Bottling machine with a set-up table and a set-up table for a bottling machine and a set-up table for a bottle handling machine;" U.S. Pat. No. 5,996,322, entitled "In-line bottling plant;" U.S. Pat. No. 5,896,899, entitled "Method and an apparatus for sterile bottling of beverages;" U.S. Pat. No. 5,848,515, entitled "Continuous-cycle sterile bottling plant;" U.S. Pat. No. 5,634,500, entitled "Method for bottling a liquid in bottles or similar containers;" and U.S. Pat. No. 5,425,402, entitled "Bottling system with mass filling and capping arrays."

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

Some examples of starwheels which may possibly be utilized or adapted for use in at least one possible embodiment may possibly be found in the following U.S. patents: U.S. Pat. No. 5,613,593, entitled "Container handling starwheel;" U.S. Pat. No. 5,029,695, entitled "Improved starwheel;" U.S. Pat. No. 4,124,112, entitled "Odd-shaped container indexing starwheel;" and U.S. Pat. No. 4,084,686, entitled "Starwheel control in a system for conveying containers."

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

Some examples of heat exchangers which may possibly be utilized or adapted for use in at least one possible embodiment may possibly be found in the following U.S. patents; U.S. Pat. No. 4,665,975, entitled "Plate type heat exchanger;" U.S. Pat. No. 6,810,948, entitled "Heat exchanger;" U.S. Pat. No. 6,799,428, entitled "Heat exchanger;" U.S. Pat. No. 6,394,179, entitled "Plate heat exchanger;" U.S. Pat. No. 6,125,649, entitled "Heat exchanger unit with conductive discs;" U.S. Pat. No. 5,579,650, entitled "Heat exchanger;" and U.S. Pat. No. 4,313,491, entitled "Coiled heat exchanger."

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

Some examples of heaters or heat exchangers, cooling systems, valves, pumps, or tanks that may be used or adapted for use in at least one possible embodiment of the present invention may be found in the following U.S. patents: U.S. Pat. No. 5,881,952, issued to inventor Macintyre on Mar. 16, 1999; U.S. Pat. No. 5,862,669, issued to inventors Davis et al. on Jan. 26, 1999; U.S. Pat. No. 5,459,890, issued to inventor Jarocki on Oct. 24, 1995; U.S. Pat. No. 5,367,602, issued to inventor Stewart on Nov. 22, 1994; U.S. Pat. No. 5,319,973, issued to inventors Crayton et al. on Jun. 14, 1994; U.S. Pat. No. 5,226,320, issued to inventors Dages et al. on Jul. 13, 1993; U.S. Pat. No. 5,078,123, issued to inventors Nagashima et al. on Jan. 7, 1992; and U.S. Pat. No. 5,068,030, issued to inventor Chen on Nov. 26, 1991.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of operating a container filling plant for filling containers comprising a plastic material with a filling material, said container filling plant comprising: a controller arrangement to monitor and control said container filling plant; a filling machine being configured and disposed to fill empty containers with a filling material; a first moving arrangement being configured and disposed to move plastic material containers to said filling machine; said filling machine comprising: a moving device being configured and disposed to accept plastic material containers from said first moving arrangement and to move plastic material containers within said filling machine; an apparatus being configured and disposed to hold plastic material containers during filling; and at least one filling device being configured and disposed to fill plastic material containers with a filling material upon the plastic material containers being within said filling machine; a closing machine being configured and disposed to close filled plastic material containers; a second moving arrangement being configured and disposed to accept filled plastic material containers from said moving device of said filling machine to move filled plastic material containers out of said filling machine; said second moving arrangement being configured and disposed to move filled plastic material containers from said filling machine to said closing machine; said closing machine comprising: a moving device being configured and disposed to accept filled plastic material containers from said second moving arrangement and to move filled plastic material containers within said closing machine; an apparatus being configured and disposed to hold filled plastic material containers during closing; and at least one closing device being configured and disposed to close filled plastic material containers upon the filled plastic material containers being within said closing machine; a treatment machine being configured and disposed to treat plastic material containers prior to filling; a third moving arrangement being configured and disposed to move plastic material containers to said treatment machine; said first moving arrangement being configured and disposed to move treated plastic material containers from said treatment machine to said filling machine; said treatment machine comprising: a moving device being configured and disposed to accept plastic material containers from said third moving arrangement and to move plastic material containers within said treatment machine; an apparatus being configured and disposed to hold plastic material containers during treating; at least one treatment device being configured and disposed to treat plastic material containers upon the plastic material containers being within said treatment machine; and said at least one treatment device comprising: a source of a treatment agent, which treatment agent is configured to be heated to treat the inside surface of a plastic material container; a heater being configured and disposed to heat a portion of said treatment agent to a temperature greater than the temperature which a plastic material container can tolerate without destructive effects on the plastic material container; a dispensing arrangement being configured to dispense at least one pulse of said heated treatment agent into a plastic material container, which said at least one pulse of heated treatment agent is at a sufficiently high temperature to distort a plastic material container if applied for a length of time, at least somewhat greater than a length of a pulse of said at least one pulse, and said at least one pulse is sufficiently long and at a sufficiently high temperature to treat the inside surface of the plastic material container, and sufficiently short to minimize distortion of the plastic material container; said controller arrangement being configured to control said dispensing arrangement to dispense at least one pulse of said heated treatment agent into a plastic material container, which said at least one pulse of heated treatment agent is at a sufficiently high temperature to distort a plastic material container if applied for a length of time, at least somewhat greater than a length of a pulse of said at least one pulse, and said at least one pulse of heated treatment agent is sufficiently long and at a sufficiently high temperature to treat the inside surface of the plastic material container, and also sufficiently short to minimize distortion of the plastic material container; and said controller arrangement being further configured to permit forming with said dispensing arrangement said at least one pulse of heated treatment agent to maximize throughput of plastic material containers and minimize treatment time of plastic material containers, said method comprising the steps of:

moving a plastic material container into said treatment machine;
  heating a portion of said treatment agent to a temperature greater than the temperature which the plastic material container can tolerate without destructive effects on the plastic material container;
  dispensing at least one pulse of said heated treatment agent into the plastic material container, which said at least one pulse of heated treatment agent is at a sufficiently high temperature to distort the plastic material container if applied for a length of time, at least somewhat greater than a length of a pulse of said at least one pulse, and said at least one pulse of heated treatment agent is sufficiently long and at a sufficiently high temperature to treat the inside surface of the plastic material container, and also sufficiently short to minimize distortion of the plastic material container;
  terminating the dispensing of said at least one pulse of said heated treatment agent into the plastic material container upon sufficient dispensing of heated treatment agent;
  controlling the dispensing and termination of the dispensing of said at least one pulse of heated treatment agent into the plastic material container;
  moving the treated plastic material container from said dispensing arrangement to said filling machine;
  filling the treated plastic material container;
  moving the treated, filled plastic material container to said closing machine;
  closing the treated, filled plastic material container;
  moving an additional plastic material container into said treatment machine;
  dispensing at least one pulse of said heated treatment agent into the additional plastic material container, which said at least one pulse of heated treatment agent is at a sufficiently high temperature to distort the plastic material container if applied for a length of time at least somewhat greater than a length of a pulse of said at least one pulse, and said at least one pulse of heated treatment agent is sufficiently long and at a sufficiently high temperature to treat the inside surface of the additional plastic material container, and also sufficiently short to minimize distortion of the additional plastic material container;
  terminating the dispensing of at least one pulse of said heated treatment agent into the additional plastic material container upon sufficient dispensing of heated treatment agent;
  controlling the dispensing and termination of the dispensing of at least one pulse of heated treatment agent into the additional plastic material container;
  moving the additional treated plastic material container from said dispensing arrangement to said filling machine;
  filling the additional treated plastic material container;
  moving the additional treated, filled plastic material container to said closing machine; and
  closing the additional treated, filled plastic material container.

2. The method according to claim 1, wherein:
said at least one pulse of heated treatment agent comprises a series of pulses separated from one another.

3. The method according to claim 2, wherein:
said dispensing arrangement comprises:
  a vertical tube;
  an actuator device being configured and disposed to move said tube from a disengaged position outside of the plastic material container to an engaged position within the plastic material container, and back again; and
  said tube is configured to be disposed in said engaged position within a plastic material container to permit a flow of heated treatment agent within the plastic material container.

4. The method according to claim 3, wherein:
said plastic material containers comprise polyethylene terephthalate.

5. The method according to claim 4, wherein said treatment agent comprises hydrogen peroxide to sterilize plastic material containers in preparation for filling.

6. The method according to claim 5, wherein the treatment agent is heated to a temperature in the range between about one hundred thirty degrees Celsius and about one hundred fifty degrees Celsius.

7. A container filling plant for filling containers comprising polyethylene terephthalate with liquid, said container filling plant comprising:
  a controller arrangement to monitor and control said container filling plant;
  a container filling machine being configured and disposed to fill polyethylene terephthalate containers with liquid;
  a first conveyor arrangement being configured and disposed to convey polyethylene terephthalate containers to be filled to said container filling machine;
  said container filling machine comprising:
    a rotor;
    a rotatable vertical machine column;

said rotor being connected to said vertical machine column to permit rotation of said rotor about said vertical machine column;

a plurality of container filling elements for filling polyethylene terephthalate containers with liquid being disposed on the periphery of said rotor;

each of said plurality of container filling elements comprising a container carrier being configured and disposed to receive and hold each polyethylene terephthalate container to be filled;

each of said plurality of container filling elements being configured and disposed to dispense liquid into each polyethylene terephthalate container to be filled;

at least one liquid reservoir being configured to hold a supply of liquid;

at least one supply line being configured and disposed to connect said at least one liquid reservoir to said container filling machine to supply liquid to said container filling machine;

a first star wheel structure being configured and disposed to move polyethylene terephthalate containers into said container filling machine;

a second star wheel structure being configured and disposed to move polyethylene terephthalate containers out of said container filling machine;

a container closing machine being configured and disposed to close tops of filled polyethylene terephthalate containers;

a second conveyor arrangement being configured and disposed to convey filled polyethylene terephthalate containers from said container filling machine to said container closing machine;

said container closing machine comprising:
a rotor;
a rotatable vertical machine column;
said rotor being connected to said vertical machine column to permit rotation of said rotor about said vertical machine column;
a plurality of closing devices being disposed on the periphery of said rotor;
each of said plurality of closing devices being configured and disposed to place closures on each filled polyethylene terephthalate container;
each of said plurality of closing devices comprising a container carrier being configured and disposed to receive and hold each filled polyethylene terephthalate container;
a first star wheel structure being configured and disposed to move filled polyethylene terephthalate containers into said container closing machine;
a second star wheel structure being configured and disposed to move filled, closed polyethylene terephthalate containers out of said container closing machine;

a container sterilization machine being configured and disposed to sterilize polyethylene terephthalate containers prior to filling;

a third conveyor arrangement being configured and disposed to convey sterilized polyethylene terephthalate containers from said container sterilization machine to said container filling machine said container sterilization machine comprising:
a rotor;
a rotatable vertical machine column;
said rotor being connected to said vertical machine column to permit rotation of said rotor about said vertical machine column;
a first star wheel structure being configured and disposed to move polyethylene terephthalate containers into said container sterilization machine;
a second star wheel structure being configured and disposed to move sterilized polyethylene terephthalate containers out of said container sterilization machine;
a plurality of container sterilization devices being disposed on the periphery of said rotor and being configured to sterilize the insides of polyethylene terephthalate containers prior to filling;
each of said plurality of sterilization devices comprising a container carrier being configured and disposed to receive and hold each polyethylene terephthalate container;
each of said plurality of sterilization devices comprising:
a supply for containing treatment agent of hydrogen peroxide to treat polyethylene terephthalate containers;
a spray device being configured and disposed to spray and mix compressed air with a supply of treatment agent comprising hydrogen peroxide to create treated air to treat polyethylene terephthalate containers to sterilize polyethylene terephthalate containers in preparation for filling;
a heater or heat exchanger being configured and disposed to heat treated air;
a helical heating channel being configured and disposed to heat treated air and to permit the flow of treated air there through;
a vertical tube being configured and disposed to permit a flow of treated air into a polyethylene terephthalate container;
said tube comprising a dispensing opening being configured to be disposed within a polyethylene terephthalate container to permit the flow of treated air into a polyethylene terephthalate container;
said helical heating channel being disposed about said tube;
a rod being disposed vertically and being configured and disposed to move up and down from a disengaged position outside of the polyethylene terephthalate container to an engaged position within the polyethylene terephthalate container, and back again;
said rod comprising a channel being in an operative connection with said dispensing opening in said tube;
an actuator device being configured and disposed to move said rod up and down from a disengaged position outside of the polyethylene terephthalate container to an engaged position within the polyethylene terephthalate container, and back again, thus being configured and disposed to move said tube into and out of a polyethylene terephthalate container;
a control valve system being configured and disposed to control injection of at least one pulse of treated air into a polyethylene terephthalate container;
said heater being configured and disposed to heat treated air to a temperature greater than the temperature which a polyethylene terephthalate container can tolerate without destructive effects on the polyethylene terephthalate container;
a dispensing arrangement being configured and disposed to dispense treated air into a polyethylene terephthalate container to be treated;

said dispensing arrangement being configured to dispense at least one pulse of treated air into a polyethylene terephthalate container, which said at least one pulse of heated, treated air is at a sufficiently high temperature to distort a polyethylene terephthalate container if applied for a length of time, at least somewhat greater than a length of a pulse of said at least one pulse, and said at least one pulse of heated, treated air is sufficiently long and at a sufficiently high temperature to treat the inside surface of the polyethylene terephthalate container and also sufficiently short to minimize destructive effects on the polyethylene terephthalate container; and said controller arrangement being configured to control said dispensing arrangement to dispense at least one pulse of treated air into a polyethylene terephthalate container, which said at least one pulse of heated, treated air is at a sufficiently high temperature to distort a polyethylene terephthalate container if applied for a length of time, at least somewhat greater than a length of a pulse of said at least one pulse, and said at least one pulse of treated air is sufficiently long and at a sufficiently high temperature to treat the inside surface of the polyethylene terephthalate container, and also sufficiently short to minimize destructive effects on the polyethylene terephthalate container;

said controller arrangement being configured further to permit forming with said dispensing arrangement said at least one pulse of heated, treated air to maximize throughput of polyethylene terephthalate containers and minimize treatment time of polyethylene terephthalate containers.

8. The container filling plant according to claim 7, wherein:
said at least one pulse of heated, treated air comprises a series of pulses separated from one another.

9. The container filling plant according to claim 8, wherein:
said rod can be moved axially by the actuator device in an axis parallel to a vertical treatment device axis between an idle position and a work position, in which rod an axial channel is formed that is in communication with the dispensing opening, and which has, on the end that is farther from the dispensing opening, at least one control opening, which when the rod is in the work position is in communication with the heater channel or with a chamber that is connected with said channel;

said tube that forms the dispensing opening can be fastened on the end farther from the discharge openings to one end of the rod, preferably so that it can be replaced or exchanged;

preceding the heater channel in the direction of flow there is a sprayer device for the introduction of the water mixed with hydrogen peroxide by means of at least one spray nozzle;

said heater device, comprising an electrical heater device or heater cartridge, is configured to heat the heater channel;

a plurality of treatment device heads are disposed on the periphery of a rotor that rotates around a vertical machine axis;

said heater channel is realized to heat the treatment agent to a processing temperature in the range between about one hundred thirty degrees Celsius and about one hundred fifty degrees Celsius;

said heater channel is a channel that is coiled around an axis of the treatment device head;

said heater channel is realized in a housing of a heat exchanger of the treatment device head; and said housing comprises a core which has at least one groove on its periphery that forms the heater channel.

10. A container filling plant for filling containers comprising a plastic material with a filling material, said container filling plant comprising:

a controller arrangement to monitor and control said container filling plant;

a filling machine being configured and disposed to fill empty plastic material containers with a filling material;

a first moving arrangement being configured and disposed to move plastic material containers to said filling machine;

said filling machine comprising:
a moving device being configured and disposed to accept plastic material containers from said first moving arrangement and to move plastic material containers within said filling machine;
an apparatus being configured and disposed to hold plastic material containers during filling; and
at least one filling device being configured and disposed to fill plastic material containers with a filling material upon the plastic material containers being within said filling machine;

a closing machine being configured and disposed to close filled plastic material containers;

a second moving arrangement being configured and disposed to accept filled plastic material containers from said moving device of said filling machine to move filled plastic material containers out of said filling machine;

said second moving arrangement being configured and disposed to move filled plastic material containers from said filling machine to said closing machine;

said closing machine comprising:
a moving device being configured and disposed to accept filled plastic material containers from said second moving arrangement and to move filled plastic material containers within said closing machine;
an apparatus being configured and disposed to hold filled plastic material containers during closing; and
at least one closing device being configured and disposed to close filled plastic material containers upon the filled containers being within said closing machine;

a treatment machine being configured and disposed to treat plastic material containers prior to filling;

a third moving arrangement being configured and disposed to move plastic material containers to said treatment machine;

said first moving arrangement being configured and disposed to move treated plastic material containers from said treatment machine to said filling machine;

said treatment machine comprising:
a moving device being configured and disposed to accept plastic material containers from said third moving arrangement and to move plastic material containers within said treatment machine;
an apparatus being configured and disposed to hold plastic material containers during treating;
at least one treatment device being configured and disposed to treat plastic material containers upon the plastic material containers being within said treatment machine; and
said at least one treatment device comprising:

a source of a treatment agent, which treatment agent is configured to be heated to treat the inside surface of a plastic material containers;

a heater being configured and disposed to heat a portion of said treatment agent to a temperature greater than the temperature which a plastic material container can tolerate without distortion on the plastic material container;

a dispensing arrangement being configured to dispense at least one pulse of said heated treatment agent into a plastic material container, which said at least one pulse of heated treatment agent is at a sufficiently high temperature to distort a plastic material container if applied for a substantial length of time, and said at least one pulse of said heated treatment agent is sufficiently long and at a sufficiently high temperature to treat the inside surface of the plastic material container, and sufficiently short to minimize distortion of the plastic material container, thus, to maximize throughput and minimize treatment time; and said controller arrangement being configured to control said dispensing arrangement to dispense at least one pulse of said heated treatment agent into a plastic material container, which said at least one pulse of heated treatment agent is at a sufficiently high temperature to distort a plastic material container if applied for a substantial length of time, and said at least one pulse of heated treatment agent is sufficiently long and at a sufficiently high temperature to treat the inside surface of the plastic material container, and also sufficiently short to minimize distortion of the plastic material container.

11. The container filling plant according to claim 10, wherein:

said at least one pulse of heated treatment agent comprises a series of pulses separated from one another.

12. The container filling plant according to claim 11, wherein:

said dispensing arrangement comprises a vertical tube;

including an actuator device being configured and disposed to move said tube from a disengaged position outside of the plastic material container to an engaged position within the plastic material container, and back again; and said tube is configured to be disposed within a plastic material container to permit a flow of heated treatment agent within the plastic material container during engagement.

13. The container filling plant according to claim 12, wherein:

said heater comprises at least one heater channel through which said treatment agent flows;

said injecting arrangement comprises a valve control and a dispensing opening for the timed dispensing of said heated treatment agent into a plastic material container; and said valve control comprises a control valve system and said actuator device is configured and disposed to permit a pulsed opening and closing of the valve system.

14. The container filling plant according to claim 13, wherein said heater channel is configured to heat said treatment agent to a processing temperature in the range between about one hundred thirty degrees Celsius and about one hundred fifty degrees Celsius.

15. The container filling plant according to claim 14, wherein said heater channel is a channel that is coiled around a central axis.

16. The container filling plant according to claim 15, wherein said heater comprises a heat exchanger housing disposed about and to house said heater channel.

17. The container filling plant according to claim 16, wherein a core is disposed in said heat exchanger housing which has at least one groove on its periphery that forms the heater channel.

18. The container filling plant according to claim 17, wherein said at least one treatment device comprises a rod configured and disposed be vertically moved by said actuator device between an idle position and a work position, in which rod an axial channel is formed that is in communication with the dispensing opening, and which has, on the end the is farther from the dispensing opening, at least one control opening, which when the rod is in the work position is in communication with the heater channel or with a chamber that is connected with said channel.

19. The container filling plant according to claim 18, wherein the tube that forms the dispensing opening can be fastened on the end farther from the discharge openings to one end of the rod, preferably so that it can be replaced or exchanged.

20. The container filling plant according to claim 19, wherein:

said at least one treatment device comprises a sprayer device for the introduction of water by at least one spray nozzle, said sprayer device being disposed to precede the heater channel in the direction of flow;

said heater comprises an electrical heater device or heater cartridge to heat the heater channel;

said container treatment machine comprises a plurality of treatment devices disposed on the periphery of a rotor that rotates around a vertical machine axis; and said treatment agent comprises hydrogen peroxide.

* * * * *